US00PP16487P2

(12) United States Plant Patent
Talmadge

(10) Patent No.: US PP16,487 P2
(45) Date of Patent: Apr. 25, 2006

(54) ***DIASCIA* PLANT NAMED 'BALWHISDARCO'**

(50) Latin Name: *Diascia barbarae×Diascia integerimma×Diascia mollis*
Varietal Denomination: Balwhisdarco

(75) Inventor: Paul A. Talmadge, Guadalupe, CA (US)

(73) Assignee: Ball Horticultural Company, West Chicago, IL (US)

( * ) Notice: Subject to any disclaimer, the term of this patent is extended or adjusted under 35 U.S.C. 154(b) by 47 days.

(21) Appl. No.: 11/011,321

(22) Filed: Dec. 13, 2004

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
(74) *Attorney, Agent, or Firm*—Wood, Phillips, Katz, Clark & Mortimer

(57) ABSTRACT

A new and distinct *Diascia* plant named 'Balwhisdarco' characterized by its dark coral-colored flowers, medium green-colored foliage, and vigorous, mounded, and spreading growth habit.

1 Drawing Sheet

Latin name of genus and species of plant claimed: *Diascia barbarae×Diascia integerimma×Diascia mollis.*
Variety denomination: 'Balwhisdarco'.

BACKGROUND OF THE INVENTION

The present invention relates to a new and distinct cultivar of Interspecific *Diascia* plant hereinafter referred to by the cultivar name 'Balwhisdarco'.

The new cultivar originated in a controlled breeding program during autumn 2000, at Guadalupe, Calif. The objective of the breeding program was the development of *Diascia* cultivars with a well-branched, spreading growth habit, continuous flowering, and medium green-colored foliage.

The female (seed) parent of the new cultivar was the proprietary Interspecific *Diascia* breeding selection designated 1624-1, not patented, characterized by its large pink-colored flowers and bush type habit. The male (pollen) parent of the new cultivar was the proprietary Interspecific *Diascia* breeding selection designated 1646-1, not patented, characterized by its coral-colored flowers and prostrate habit. The new cultivar was discovered and selected by the inventor as a single flowering plant within the progeny of the above stated cross in the spring of 2002.

Asexual reproduction of the new cultivar by terminal stem cuttings since spring 2002 at Guadalupe, Calif. and West Chicago, Ill. has demonstrated that the new cultivar reproduces true to type with all the characteristics, as herein described, firmly fixed and retained through successive generations of such asexual propagation.

SUMMARY OF THE INVENTION

The new cultivar has not been observed under all possible environmental conditions to date. Accordingly, it is possible that the phenotype may vary somewhat with variations in the environment, such as temperature, light intensity, and day length without, however, any variance in genotype.

The following characteristics of the new cultivar have been repeatedly observed and can be used to distinguish 'Balwhisdarco' as a new and distinct cultivar of *Diascia* plant:

1. Dark coral-colored flowers.
2. Medium green-colored foliage.
3. Vigorous, mounded, and spreading growth habit.

Plants of the new cultivar differ from plants of the female parent primarily in flower color and plant habit, and from plants of the male parent primarily in flower color and plant habit.

Of the many *Diascia* cultivars know to the inventor, the most similar to the new cultivar is the cultivar Diastina, U.S. Plant Pat. No. 13,932. However, in side-by-side comparisons, plants of the new cultivar differed from plants of 'Diastina' in the following characteristics:

1. Plants of the new cultivar have smaller flowers than plants of 'Diastina'.
2. Plants of the new cultivar have smaller leaves than plants of 'Diastina'.
3. The flowers of the new cultivar are a different color than those of 'Diastina'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the values cited in the detailed description, which accurately describes the colors of 'Balwhisdarco'. The plants were grown for 11 weeks in a greenhouse at West Chicago, Ill.

DETAILED BOTANICAL DESCRIPTION

Figure 1:
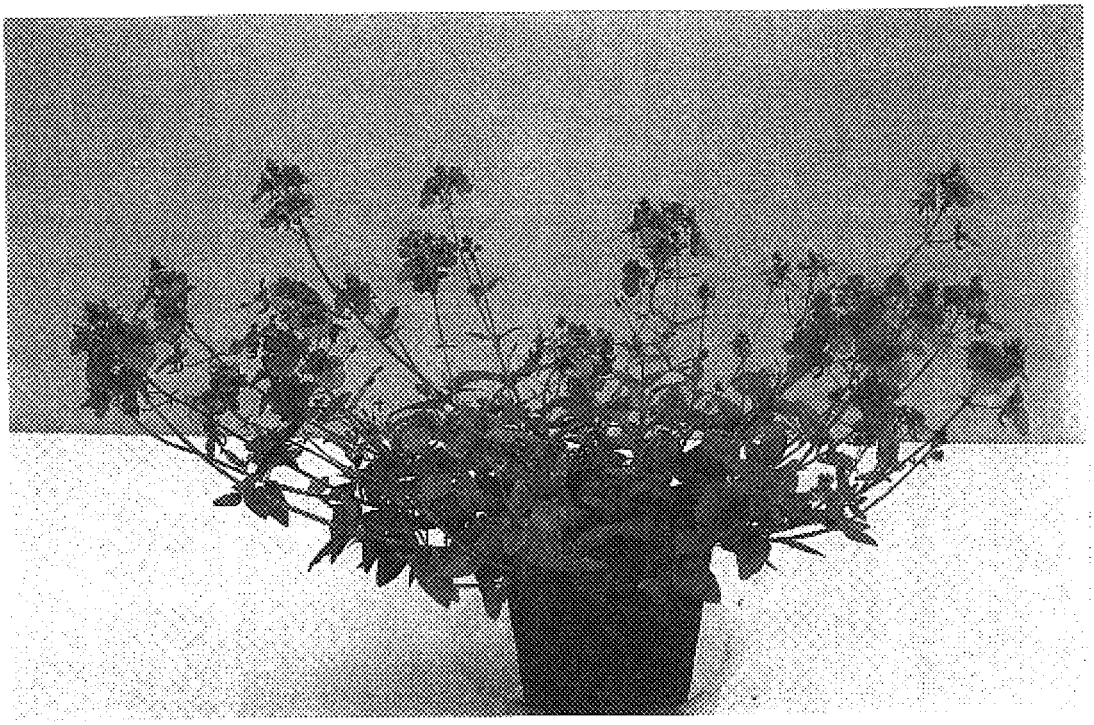
FIG. 1 illustrates a side view of the overall growth and flowering habit of 'Balwhisdarco'.
Figure 2:
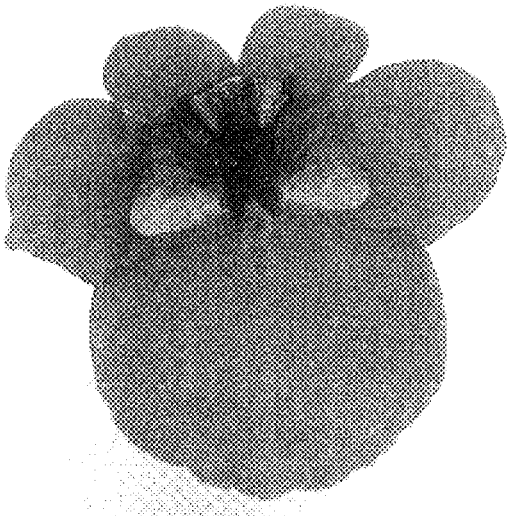
FIG. 2 illustrates a close-up view of an individual flower of 'Balwhisdarco'.

The chart used in the identification of colors described herein is The R.H.S. Colour Chart of The Royal Horticultural Society, London, England, 2001 edition, except where general color terms of ordinary significance are used. The color values were determined on Oct. 9, 2004 between 10:00 and 11:00 a.m. under natural light conditions.

The following descriptions and measurements describe plants produced from terminal stem cuttings of stock plants and grown in a double polycarbonate-covered greenhouse under conditions comparable to those used in commercial practice. The plants were grown at West Chicago, Ill. in 10 cm pots for 11 weeks while utilizing a soilless growth medium. Greenhouse temperatures were maintained at approximately 62°–75° F. (17°–24° C.) during the day and approximately 52°–60° F. (11°–15° C.) during the night. Greenhouse light levels were maintained at 5,000 to 8,000 footcandles during the day.

Botanical classification: Interspecific *Diascia* cultivar Balwhisdarco.

Parentage:

*Female parent.*—Proprietary Interspecific *Diascia* breeding selection designated 1624-1, not patented.

*Male parent.*—Proprietary Interspecific *Diascia* breeding selection designated 1646-1, not patented.

Propagation:

*Type cutting.*—Terminal stem cutting.

*Time to initiate roots.*—Approximately 6 to 9 days.

*Time to produce a rooted cutting.*—Approximately 3 to 4 weeks.

*Root description.*—Fine, fibrous.

*Rooting habit.*—Freely branching.

Plant description:

*Crop time.*—Approximately 5 to 7 weeks from planting of a rooted cutting in a 10 cm pot.

*Habit of growth.*—Vigorous. Freely branching with branches forming at every node.

*Form.*—Spreading, trailing.

*Size.*—Height: Approximately 19.9 cm. Diameter (area of spread): Approximately 47.9 cm.

*Branch description.*—Quantity: Approximately 29 flowering branches. Strength: Moderate. Shape: Square in cross section. Length: Approximately 28 cm. Diameter: Approximately 1.8 mm. Internode length at middle of branch: Approximately 3.5 cm. Texture: Glabrous. Color: 144A.

*Foliage.*—Quantity per branch: Approximately 9. Fragrance: Slight. Type: Simple. Arrangement: Opposite. Leaf orientation to stem: Right angle. Shape: Ovate. Apex: Acute. Base: Cordate. Margin: Broadly serrate. Venation pattern: Pinnate. Leaf length: Approximately 1.7 cm. Leaf width: Approximately 1 cm. Texture of upper and lower surfaces: Glabrous. Color of mature foliage: Upper surface: 137A with venation of 144C. Lower surface: 138B with venation of 144C. Petiole length: Approximately 8 mm. Petiole diameter: Approximately 0.8 mm. Petiole texture: Upper and lower surfaces: Glabrous. Petiole color: 144C.

Flowering description:

*Time to first flower.*—Approximately 5–7 weeks after planting of rooted cutting.

*Flowering habit.*—Freely flowering.

Inflorescence description:

*Appearance.*—Type: Terminal clusters.

*Size.*—Length (depth): Approximately 4.4 cm. Width: Approximately 5 cm.

Flower description:

*Lastingness of a single bloom.*—Approximately 4–5 days.

*Quantity per inflorescence.*—Approximately 6.

*Type.*—Solitary, not persistent, five lobed, zygomorphic, with two nectar spurs.

*Fragrance.*—None.

*Aspect.*—Concave.

*Shape.*—Obovate.

*Flower size.*—Width: Approximately 1.6 cm. Length: Approximately 1.7 cm. Depth: Approximately 8 mm.

*Petals.*—Quantity: Five, two upper petals and three lower petals. Type: Imbricate, fused at base. Aspect: Cupped. Apex: Obtuse. Margin: Entire. Appearance: Iridescent. Color: Upper and lower surfaces: Closest to but lighter than 39A. Indentation at base of upper petals: Length: 3 mm. Width: 3 mm. Color: 3A.

*Two upper (banner) petals.*—Length: Approximately 7.3 mm. Width: Approximately 4 mm. Texture of upper and lower surface: Glabrous.

*Lateral petals.*—Length: Approximately 6.5 mm. Width: Approximately 6.5 mm. Texture of upper and lower surface: Glabrous. Sharply curved nectar spurs form at base of each of the lateral petals.

*Nectar spurs.*—Length: Approximately 7 mm. Diameter at base: 3 mm. Diameter at tip: 0.7 mm. Texture: Glabrous. Color: 51B.

*Lower petal.*—Length: Approximately 1 cm. Width: Approximately 1.1 cm. Texture of upper surface: Glabrous except glandular where petals are fused. Gland color: N186A. Texture of lower surface: Glabrous.

*Sepals.*—Quantity: 5. Shape: Lanceolate. Apex: Acute. Margin: Entire. Length: Approximately 4 mm. Width: Approximately 1 mm. Texture: Upper/inner surface: Glabrous. Outer/lower surface: Moderately glandular pubescent. Glands are colorless and translucent. Color of upper and lower surface is 143B.

*Calyx.*—Shape: Five pointed star. Length: Approximately 3 mm. Diameter. Approximately 6 mm.

*Peduncle.*—Strength: Strong. Aspect: At acute angle to stem. Length: Approximately 2 cm. Diameter: Approximately 0.5 mm. Texture: Moderately stipulate glandular. Glands are colorless and translucent. Color: 143B with overlay of 183B.

*Bud (at first color).*—Shape: Globular. Length: Approximately 5 mm in length. Diameter: Approximately 5 mm. Texture: Stipulate glandular. Color: 51B.

*Reproductive organs.*—Androecium: There are 4 stamens per flower. Filament length: 3.6 mm. Filament color: Between 79B and 79C. Filament texture: Glandular. Anther shape: Oval. Anther length: 0.8 mm. Anther color: 12C. Pollen amount: Abundant. Pollen color: 13A. Gynoecium: Pistil number: One per flower. Pistil length: 4 mm. Stigma shape: Round. Stigma length: 0.3 mm. Stigma color: 5C. Style length: Approximately 1.7 mm. Ovary length: Approximately 2 mm. Ovary color: 143C. Ovary texture: Glabrous.

Seed and fruit production: Neither seed nor fruit production has been observed.

Disease and pest resistance: Resistance to pathogens or pests common to *Diascia* has not been observed.

What is claimed is:

1. A new and distinct cultivar of Interspecific *Diascia* plant named 'Balwhisdarco', substantially as herein shown and described.

* * * * *